United States Patent [19]

LeBlanc et al.

[11] Patent Number: 4,876,396

[45] Date of Patent: Oct. 24, 1989

[54] SELECTIVE CHLORINATION OF PHENOLS

[75] Inventors: Jean-Claude LeBlanc, Grenoble; Serge Ratton, Villefontaine, both of France

[73] Assignee: Rhone-Poulenc Specialites Chimiques, Courbevoie, France

[21] Appl. No.: 78,771

[22] Filed: Jul. 28, 1987

Related U.S. Application Data

[63] Continuation-in-part of Ser. No. 909,177, Sep. 19, 1986, abandoned.

[30] Foreign Application Priority Data

Sep. 19, 1985 [FR] France ............................. 85 14093
Sep. 3, 1986 [EP] European Pat. Off. ....... 86.420221.3

[51] Int. Cl.$^4$ ..................... C07C 37/62; C07C 39/24
[52] U.S. Cl. ................................. 568/779; 560/129; 568/308; 568/425; 568/655
[58] Field of Search ................. 568/779, 776, 774

[56] References Cited

U.S. PATENT DOCUMENTS

4,237,321 12/1980 Cuthbertson ..................... 568/789

FOREIGN PATENT DOCUMENTS

0196260 10/1986 European Pat. Off. ............ 568/779
3318791 12/1983 Fed. Rep. of Germany ...... 568/779
2135310 8/1984 United Kingdom ................ 568/776

OTHER PUBLICATIONS

Nodera et al., "Chemical Abstracts", vol. 93 (1980), p. 93:239023s.

Primary Examiner—Werren B. Lone
Attorney, Agent, or Firm—Burns, Doane, Swecker & Mathis

[57] ABSTRACT

Phenolic compounds and mixtures thereof, e.g., admixture of 2,4-dichlorophenol and 2,6-dichlorophenol, are selectively chlorinated at a position ortho to a hydroxyl function thereof, by reacting such phenolic compound with gaseous chlorine, in a molten reaction medium, in the presence of a catalytically effective amount of a primary, secondary or tertiary amine.

13 Claims, No Drawings

SELECTIVE CHLORINATION OF PHENOLS

CROSS REFERENCE TO RELATED APPLICATIONS

This application is a continuation-in-part of co-pending U.S. patent application Ser. No. 909,177 filed Sept. 19, 1986 now abandoned.

BACKGROUND OF THE INVENTION

1. Field of the Invention

The present invention relates to the selective chlorination of phenolic compounds with gaseous chlorine, in the ortho-position relative to the hydroxyl group.

2. Description of the Prior Art

In the preparation of chlorophenols by chlorination of phenol, isomers are produced at different stages of the reaction, ultimately giving rise to many different compounds, which must then be separated by procedures which are both expensive and difficult. Moreover, the ratios of the different isomers do not necessarily correspond to those which would be economically viable, taking into account the existing markets.

Therefore, it appeared desirable to provide selective chlorination processes, especially for selective chlorination in the ortho-position, or in the para-position, relative to the hydroxyl group of the phenolic compound.

Thus, published German patent application No. 3,318,791 describes a selective process for the chlorination of phenol into 2-chlorophenol, in a perchlorinated apolar solvent and in the presence of a branched amine.

However, the use of a solvent in an industrial chlorination process is ofttimes problematical, providing such difficulties as, for example, the need for a larger reactor volume and a more difficult separation of the reaction products.

SUMMARY OF THE INVENTION

Accordingly, a major object of the present invention is the provision of improved process for the selective chlorination of phenolic compounds with gaseous chlorine, one wherein the reaction is carried out in a molten reaction medium and in the presence of an amine.

Briefly, the present invention features a process for the selective chlorination, in the ortho-position relative to the hydroxyl group, of phenolic compounds having the general formula (I):

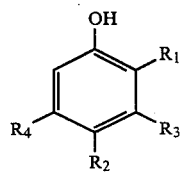

in which $R_2$ is a halogen atom; an alkyl group having from 1 to 4 carbon atoms; an alkoxy group having from 1 to 4 carbon atoms; an acyloxy group having from 2 to 4 carbon atoms; an acyl group having from 2 to 4 carbon atoms; a carboxylic acid group; an ester group —$COOR_5$, wherein $R_5$ is a straight or branched chain alkyl radical having from 1 to 4 carbon atoms; a nitrile group; an OH group; or a —CHO group; $R_1$ is a hydrogen atom or one of the substituents $R_2$; $R_3$ and $R_4$, which may be identical or different, are each a hydrogen atom or one of the substituents $R_2$; in a molten reaction medium, with gaseous chlorine, and wherein the reaction is carried out in the presence of a catalytically effective amount of a primary, secondary or tertiary amine.

The term "amine" is defined as any compound, liquid or solid under the operating conditions of the process, which comprises one or several amine functions.

Such a compound may also contain one or several other functional groups, such as, for example, hydroxyl, carboxylic acid, carboxylic acid ester, amide or imine.

Ammonia is also considered to be an amine for purposes of the present invention.

The amines used may also be introduced in the form of their respective chlorohydrates.

DETAILED DESCRIPTION OF THE PREFERRED EMBODIMENTS OF THE INVENTION

More particularly according to the present invention, the amine catalysts are advantageously amines of the formula (II):

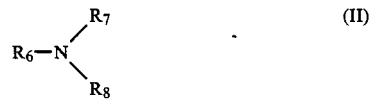

in which $R_6$, $R_7$ and $R_8$, which may be identical or different, are each a straight-chain alkyl radical having from 3 to 12 carbon atoms, or a tertiary alkyl radical having from 4 to 12 carbon atoms, with the proviso that such alkyl radicals may contain one or two oxygen bridges, —O—, or a hydroxyl, amine, carboxylic acid, carboxylic acid ester, amide or imine group; a phenyl radical, a cyclohexyl radical, a cycloheptyl radical, a cyclopentyl radical, or a phenylalkyl, cyclohexylalkyl, cycloheptylalkyl or cyclopentylalkyl radical, the alkyl part of which comprises 1 to 4 carbon atoms; and with the further provisos that one or two of the substituents $R_6$, $R_7$ and $R_8$ may be hydrogen atom; $R_6$ may be an —$NH_2$ group; $R_7$ and $R_8$ may together form, with the nitrogen atom from which they depend, a heterocycle which is saturated or contains one or several double bonds, or substituted such heterocycle bearing one or more alkyl substituents having from 1 to 4 carbon atoms; $R_6$, $R_7$ and $R_8$ may together form with the nitrogen atom from which they depend, an unsaturated heterocycle, or a substituted such heterocycle bearing one or two methyl or ethyl substituents; $R_7$ and $R_8$ or $R_6$, $R_7$ and $R_8$ may together form, with the nitrogen atom from which they depend, and with one or several additional nitrogen atoms and/or oxygen atoms, a saturated or unsaturated heterocycle, optionally substituted by one or several alkyl groups having from 1 to 4 carbon atoms; and $R_7$ and $R_8$ or $R_6$, $R_7$ and $R_8$ may together form, with the nitrogen atom from which they depend, and optionally with one or several nitrogen atoms and/or oxygen atoms, a saturated or unsaturated polycyclic compound, optionally substituted by one or several alkyl groups having 1 to 4 carbon atoms.

Exemplary of such catalytically effective amines of formula (II), the following are representative:

(a) primary amines, such as n-propylamine, isopropylamine, isobutylamine, n-butylamine, tert-butylamine, n-pentylamine, 2-methylbutylamine, 3-methylbutylamine, n-hexylamine, 2-ethylhexylamine, aniline, laurylamine, cyclohexylamine, cyclopentylamine, benzylamine, guanidine, acetamidine, glycine ethyl ester, ethanolamine, ethylenediamine, hexamethylenediamine, N-aminoethylpyrrolidine, pyrazoline, lysine, N-aminoethylpyrrolidine, lysine, N-aminomorpholine and N-aminopiperidine;

(b) secondary amines, such as dibutylamine, dipropylamine, methylpropylamine, methylbutylamine, methylisobutylamine, methyltert-butylamine, methylbenzylamine, piperidine, diisopropylamine, diisobutylamine, ditert-butylamine, 1-methylcyclopentylamine, 1-methylcyclohexylamine, dicyclohexylamine, morpholine, imidiazole, pyrrolidine, imidazolidine, piperazine, and indole;

(c) tertiary amines, such as triethylamine, tributylamine, pyridine, tris(3,6-dioxaheptyl)amine and 1,8-diaza-bicyclo[5,4,0]7-undecene;

(d) ammonia;

(e) amino compounds such as hydrazine or its derivatives, in particular derivatives obtained by the substitution of one or two hydrogen atoms by alkyl, aryl, cycloaliphatic or heterocyclic radicals.

The catalytically effective amount of the amine used in the process of the invention may vary over very wide limits.

Typically it constitutes, by weight relative to the weight of the reaction mixture, from 0.005% to 5% thereof. Preferably, from 0.01 to 2.0% by weight of the amine relative to the reaction mixture will be employed, in order to provide sufficient efficacy, without using an excessive amount of the amine which does not concurrently permit any additional benefit or advantage.

Among the amines having the general formula (II), it is preferred to use primary or secondary amines of the general formula (III):

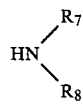

(III)

in which $R_7$ and $R_8$, which may be identical or different, are each a hydrogen atom, with the proviso that both $R_1$ and $R_8$ are not hydrogen; a straight-chain alkyl radical having from 1 to 10 carbon atoms; a secondary alkyl radical having from 3 to 10 carbon atoms; a tertiary alkyl radical having from 4 to 10 carbon atoms; a cyclohexyl or cyclopentyl radical; a phenyl radical; or a benzyl or phenethyl radical;

$R_7$ and $R_8$ may alternatively form, together with the nitrogen atom from which they depend, and with another nitrogen atom and/or oxygen atom, a heterocycle which is saturated or which has one or several double bonds. Either or both $R_7$ and $R_8$ may contain one or several amine, hydroxyl or carboxylic ester groups.

Exemplary of primary amines of the general formula (III), n-propylamine, isopropylamine, n-butylamine, isobutylamine, tert-butylamine, n-pentylamine, 2-methylbutylamine, 3-methylbutylamine, n-hexylamine, 2-methylpentylamine, 3-methylpentylamine, 2-ethylhexylamine, laurylamine, cyclohexylamine, cyclopentylamine, benzylamine, glycine ethyl ester and ethanolamine are representative.

More particularly with regard to the secondary amines of the general formula (III), those in which at least one of the substituents $R_7$ and $R_8$, and preferably both substituents $R_7$ and $R_8$ are as follows, are even more especially preferred:

a secondary alkyl radical having from 3 to 10 carbon atoms, such as isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl and 5-decyl; a cyclohexyl or cyclopentyl radical.

Also especially preferred are heterocycles where $R_7$ and $R_8$ form, together with the nitrogen atom from which they depend, a heterocycle optionally containing another nitrogen or oxygen atom.

Exemplary of such secondary amines, diisopropylamine, diisobutylamine, dicyclohexylamine, morpholine and imidazole are representative.

Also preferred are hexamethylenediamine, N-aminoethylpyrrolidine, pyrazoline, N-aminomorpholine and N-amino piperidine.

The phenolic compounds of the formula (I), for which the subject process is most valuable, are those in which $R_2$ is a chlorine atom, a fluorine atom or a bromine atom; a methoxy or ethoxy group; an aldehyde group; an OH group; a CN group; an acetoxy group; an ester group —COOR$_5$, wherein $R_5$ is a methyl or ethyl group; or an acyl group having from 2 to 4 carbon atoms; $R_1$ is a hydrogen atom, a methyl, ethyl, propyl, isopropyl or tert-butyl group, or one of the substituents $R_2$; at least one of $R_3$ and $R_4$ is a hydrogen atom, and the other either a hydrogen atom or one of the substituents $R_2$.

Exemplary of the phenolic compounds of the formula (I), representative are: 4-chlorophenol, 2,4-dichlorophenol, 3,4-dichlorophenol, 2-chloro-4-fluorophenol, 4-chloro-2-fluorophenol, 2-bromo-4-chlorophenol, 4-bromo-2-chlorophenol, 2-chloro-4-methoxyphenol, 4-chloro-2-methoxyphenol, 4-chloro-2-methylphenol, 4-methoxyphenol, 4-ethoxyphenol, 4-hydroxyacetophenone, 4-hydroxybenzonitrile, 3-chloro-4-hydroxybenzaldehyde, and 5-chloro-2-hydroxybenzaldehyde.

The process according to this invention has several advantages.

One of these advantages is its intramolecular selectivity; when it is applied to a phenolic compound of formula (I) in which at least one of the meta-positions of the hydroxyl group is unsubstituted, essentially only the ortho-positions of the OH are chlorinated, whereas in the absence of the amine, a not insignificant amount of 3-chlorophenol or of the corresponding 5-chlorophenol is always formed, which is then very difficult to separate. Additionally, these compounds may be disadvantageous for certain applications.

Another very valuable advantage relates to the intermolecular selectivity of the process: if the process is employed with a mixture of a phenolic compound of formula (I) and one or more other phenolic compounds (such as, for example, position isomers of said phenolic compound of formula (I)) which do not correspond to the formula (I), it is mostly the phenolic compound of formula (I) which is chlorinated, whereas the other phenolic compound(s) are but slightly modified.

Thus, for example, the process of the invention may advantageously be applied to a mixture of 2,4-dichlorophenol and 2,6-dichlorophenol; 2,4,6-trichlorophenol is obtained from 2,4-dichlorophenol, whereas the 2,6-dichlorophenol, which is only slightly modified, may be relatively easily separated from the final reaction mixture.

It is also possible to use an industrial crude mixture containing 2,4-dichlorophenol, 2,6-dichlorophenol and 2,4,6-trichlorophenol, and thereby obtain, as before, 2,4,6-trichlorophenol and 2,6-dichlorophenol, which may be separated by fractional distillation.

Finally, another advantage of the subject process is the fact that the reaction of the gaseous chlorine and of the phenolic compound of the formula (I) is substantially complete, whereas, in the absence of the amine, a significant amount of the chlorine does not react. The problems of recycling of the excess chlorine, or of treating the gaseous effluents become less difficult to solve.

As a result, the amount of chlorine used in the process of the invention principally depends upon the desired degree of conversion of the phenolic compound (I).

The chlorine may be used as such, or diluted with an inert gas, such as, for example, nitrogen. The presence of an inert gas makes it possible, if required, to increase the rate of gas flow without increasing the amount of chlorine introduced over a given period of time.

The temperature at which the process of the invention is carried out is generally less than or equal to 150° C. Moreover, the lower limit of the temperature zone depends on the melting point of the phenolic compound (I), or mixture of phenolic compounds.

This temperature typically ranges from the melting point of the reaction mixture to 120° C., these limits, however, not being critical.

In order to further illustrate the present invention and the advantages thereof, the following specific examples are given, it being understood that same are intended only as illustrative and in nowise limitative.

EXAMPLE 1

The following materials were introduced into a 100-cm$^3$ glass reactor equipped with a stirrer, a tube for the supply of chlorine gas, a thermometer and fitted with a condenser:
 (i) 2,4-dichlorophenol: 21.19 g (130 millimoles);
 (ii) 2,6-dichlorophenol: 21.19 g (130 millimoles);
 (iii) diisopropylamine: 0.042 g (0.42 millimole, which was 0.1% by weight of the reaction medium).

The temperature was raised to 70° C. under stirring, such that the mixture was liquid and the introduction of gaseous chlorine was then initiated at a flow rate of 5 liters/hour.

The period for which the chlorination was carried out at 70° C. was 38 minutes, which corresponded to 3.15 liters of chlorine introduced (140.6 millimoles). The experiment was therefore carried out with an 8% excess of chlorine relative to 2,4-dichlorophenol.

Upon completion of the reaction, the entire equipment was purged with a stream of nitrogen. A reaction mass of 47.21 g was obtained, which was analyzed by gas chromatography in the presence of an internal standard.

The following results were obtained:
Degree of conversion (DC) of 2,4-dichlorophenol: 99.6%
Degree of conversion (DC) of 2,6-dichlorophenol: 6.6%
Yield (Y) of 2,4,6-trichlorophenol relative to the dichlorophenols converted: 100%

$$\text{ratio } \frac{DC \text{ of the 2,4-dichlorophenol}}{DC \text{ of the 2,6-dichlorophenol}} = 15.1$$

EXAMPLE 2

The following materials were introduced into a 200-cm$^3$ glass reactor equipped as indicated in Example 1:
 (i) 2,4-dichlorophenol: 109.15 g (669.6 millimoles);
 (ii) 2,6-dichlorophenol: 24.78 g (152 millimoles);
 (iii) diisopropylamine: 0.13 g (1.29 millimole, which was 0.1% by weight of the reaction medium).

15 liters of chlorine (669.6 millimoles), which corresponded to the stoichiometric amount relative to the 2,4-dichlorophenol were introduced at 70° C., under stirring, at a flow rate of 5 l/h.

By chromatographic analysis upon completion of the chlorination, the following results were obtained:
DC of the 2,4-dichlorophenol: 99.95%
DC of the 2,6-dichlorophenol: 8.1%
Y of 2,4,6-trichlorophenol relative to the dichlorophenols converted: 99.1%

$$\text{ratio } \frac{DC \text{ of the 2,4-dichlorophenol}}{DC \text{ of the 2,6-dichlorophenol}} = 12.3$$

EXAMPLE 3 TO 6

The reaction was carried out as in Example 1 at 70° C., with a 50/50 mixture of 2,4-dichlorophenol and 2,6-dichlorophenol. The gaseous chlorine was introduced at a flow rate of 5 l/h and the amount introduced was such that the molar ratio of chlorine: 2,4-dichlorophenol was 0.95.

The following materials were introduced:
 (i) 2,4-dichlorophenol: 21.19 g (130 millimoles);
 (ii) 2,6-dichlorophenol: 21.19 g (130 millimoles);
 (iii) diisopropylamine: variable amount (see Table 1);
 (iv) chlorine: 2.765 liters (123 millimoles).

The characteristics of the different examples and the results obtained are reported in Table I:

TABLE I

| EXAMPLES | Diisopropylamine weight in g % by weight/DCP | DC of the 2,4-DCP (*) | DC of the 2,6-DCP () | Y of 2,4,6-TCP (*) | DC of the 2,4-DCP/DC of the 2,6-DCP |
|---|---|---|---|---|---|
| Control experiment A | 0 | 47.1% | 38.6% | 97.2% | 1.2 |
| Example 3 | 0.01 g 0.0235% | 73.8% | 10.0% | 100% | 7.4 |
| Example 4 | 0.042 g 0.10% | 87.0% | 4.7% | 100% | 18.5 |
| Example 5 | 0.094 g 0.225% | 82.2% | 3.8% | 100% | 21.6 |
| Example 6 | 0.84 g | 83.5% | 7.2% | 100% | 11.6 |

TABLE I-continued

| EXAMPLES | Diisopropyl-amine weight in g % by weight/ DCP | DC of the 2,4-DCP (*) | DC of the 2,6-DCP () | Y of 2,4,6-TCP (*) | DC of the 2,4-DCP/DC of the 2,6-DCP |
|---|---|---|---|---|---|
| | 2.0% | | | | |

(*) = DC of the 2,4-dichlorophenol
(**) = DC of the 2,6-dichlorophenol
(***) = Y of 2,4,6-trichlorophenol These experiments demonstrate the favorable effect of the amine used at very different amine/reaction mixture gravimetric ratios:

EXAMPLES 7 TO 11

These experiments were carried out with different amines used at the same gravimetric concentration (0.02% relative to the dichlorophenols).

The reaction was carried out as in the series of Examples 3 to 6, using the following charges:

(i) 2,4-dichlorophenol: 21.19 g (130 millimoles);
(ii) 2,6-dichlorophenol: 21.19 g (130 millimoles);
(iii) amine: 0.02% by weight relative to the dichlorophenols;
(iv) chlorine: 2.766 liters (123 millimoles).

The characteristics of the different examples and the results obtained (Example 3 is repeated for comparison) are reported in Table II:

TABLE II

| EXAMPLES | Amine used | DC of the 2,4-DCP | DC of the 2,6-DCP | Y of 2,4,6-TCP | DC of the 2,4-DCP/ DC of the 2,6-DCP |
|---|---|---|---|---|---|
| Example 3 | diisopropyl-amine | 73.8% | 10.0% | 100% | 7.4 |
| Example 7 | methyl-n-butylamine | 69.9% | 15.8% | 100% | 4.4 |
| Example 8 | dicyclohexyl-amine | 76.9% | 14.2% | 99.0% | 5.4 |
| Example 9 | tributyl-amine | 53.0% | 33.1% | 98.6% | 1.6 |
| Example 10 | tris(3,6-dioxa-heptyl)amine | 60.45% | 25.1% | 100% | 2.4 |
| Example 11 | pyridine | 60.4% | 29.2% | 97.6% | 2.1 |

At equal gravimetric concentration, a larger effect of the secondary amines relative to the tertiary amines was evidenced.

EXAMPLES 12 AND 13

These experiments were carried out with three different amines, used at the same molar concentration (0.15% to 0.18% in moles relative to the dichlorophenols).

The reaction was carried out as in the series of Examples 3 to 6, using the following charges:

(i) 2,4-dichlorophenol: 21.19 g (130 millimoles);
(ii) 2,6-dichlorophenol: 21.19 g (130 millimoles);
(iii) amine: 2.766 liters (123 millimoles).

The characteristics of the different examples and the results obtained (Example 4 is repeated for comparison) are reported in Table III:

TABLE III

| EXAMPLES | Amine % in moles/DCP (% by weight/ DCP) | DC of the 2,4-DCP | DC of the 2,6-DCP | Y of 2,4,6-TCP | DC of the 2,4-DCP/ DC of the 2,6-DCP |
|---|---|---|---|---|---|
| Example 4 | diisopropyl-amine 0.18% in moles (0.1% by weight) | 87.0% | 4.7% | 100% | 18.5 |
| Example 12 | dicyclohexyl-amine 0.18% in moles (0.2% by weight | 89.0% | 5.15% | 99.4% | 17.3 |
| Example 13 | tris(3,6-dioxa-heptyl)amine 0.155% in moles (0.3% by weight) | 75.8% | 17.25% | 99.3% | 4.4 |

EXAMPLE 14

The reaction was carried out as in the series of Examples 3 to 6, using the following charges:

(i) 2,4-dichlorophenol: 21.19 g (130 millimoles);
(ii) 2,6-dichlorophenol: 21.19 g (130 millimoles);
(iii) diisopropylamine: 0.042 g (0.42 millimole, which is, 0.1% by weight relative to the dichlorophenols);
(iv) chlorine: 2.766 liters (123 millimoles).

The characteristics of the example and the results obtained (Example 4 is repeated for comparison) are reported in Table IV:

TABLE IV

| EXAMPLES | Temperature | DC of the 2,4-DCP | DC of the 2,6-DCP | Y of 2,4,6-TCP | DC of the 2,4-DCP/ DC of the 2,6-DCP |
| --- | --- | --- | --- | --- | --- |
| Example 4 | 70° C. | 87.0% | 4.7% | 100% | 18.5 |
| Example 14 | 100° C. | 88.3% | 4.55% | 99.9% | 19.4 |

EXAMPLE 15

The following materials were introduced into a 200-cm$^3$ glass reactor equipped with a stirrer, a tube for the supply of gaseous chlorine, a thermometer and fitted with a condenser:
 (i) 2,4-dichlorophenol: 100 g (613.5 millimoles);
 (ii) diisopropylamine: 0.10 g (1 millimole, which was 0.1% by weight of the reaction medium).

The temperature was raised to 70° C., under stirring, such that the mixture was liquid and the introduction of gaseous chlorine was initiated at a flow rate of 5 liters/hour.

The period of chlorination carried out at 70° C. was 3 hours, which corresponded to 670 millimoles of chlorine introduced. The reaction was therefore carried out with a 10% excess of chlorine relative to the 2,4-dichlorophenol.

Upon completion of the reaction, the entire equipment was purged with a stream of nitrogen. A reaction mass was obtained, which was analyzed by gas chromatography in the presence of an internal standard.

The following results were obtained:
 2,4-Dichlorophenol remaining: 0.09 g, which amounted to a DC of 99.9%
 2,4,6-Trichlorophenol obtained: 119.69 g, which amounted to a Y relative to the 2,4-chlorophenol converted of 98.9%
 2,4,5-Trichlorophenol concentration: less than 0.001% by weight in the reaction mass (estimated at 0.0007%).

EXAMPLE 16

Example 15 was repeated, with a twenty times higher concentration of diisopropylamine.

Thus, the following charges were used:
 (i) 2,4-dichlorophenol: 100 g (613.5 millimoles);
 (ii) diisopropylamine: 2.0 g (20 millimoles, which was 2% by weight of the reaction medium).

The following results were obtained:
 2,4-Dichlorophenol remaining: 0.08 g, which amounted to a DC of 99.9%
 2,4,6-Trichlorophenol obtained: 121.05 g, which amounted to a Y relative to the 2,4-dichlorophenol converted of 100%
 2,4,5-Trichlorophenol concentration: less than 0.001% by weight in the reaction mass (estimated at 0.0004%).

EXAMPLES 17 AND 18

The reaction was carried out as in the series of Examples 3 to 6, using the following materials:
 (i) 2,4-dichlorophenol: 21.19 g (130 millimoles);
 (ii) 2,6-dichlorophenol: 21.19 g (130 millimoles);
 (iii) amine (see table): 0.042 g (0.1 by weight relative to the dichlorophenols);
 (iv) chlorine (flow rate 5 l/h): Example 17=2.750 liters (123 millimoles)
 (v) Example 18=2.910 liters (130 millimoles).

The characteristics of the two examples and the results obtained are reported in Table V.

TABLE V

| EXAMPLES | Amine used % by weight/ DCP | DC of the 2,4-DCP | DC of the 2,6-DCP | Y of 2,4,6-TCP | DC of the 2,4-DCP/ DC of the 2,6-DCP |
| --- | --- | --- | --- | --- | --- |
| Example 17 | isopropylamine 0.1% by weight | 87.45% | 6.55% | 98.7% | 13.3 |
| Example 18 | n-propylamine 0.1% by weight | 94.9% | 6.8% | 98.5% | 13.9 |

CONTROL EXPERIMENT B

Example 15 was repeated without diisopropylamine.
In order to obtain a sufficient degree of conversion of the 2,4-dichlorophenol, a 60% excess of chlorine relative to the stiochiometric quantity should be introduced.

The following results were obtained:
 2,4-Dichlorophenol remaining: 0.94 g, which amounted to a DC of 99.05%
 2,4,6-Trichlorophenol obtained: 120.89 g, which amounted to a Y relative to the 2,4-dichlorophenol converted of 100%
 2,4,5-Trichlorophenol concentration: 0.003% by weight in the reaction mass.

CONTROL EXPERIMENT C

Control experiment B was repeated, but the supply of chlorine was terminated when the molar ratio of chlorine introduced/2,4-dichlorophenol added was equal to 1.1 (which represented a 10% excess of chlorine relative to the stoichiometric quantity).

The following results were obtained:
 DC of 2,4-Dichlorophenol: 91.0%
 Y of 2,4,6-Trichlorophenol: 100%
 2,4,5-Trichlorophenol concentration: 0.0087% by weight in the reaction mass.

EXAMPLES 19 TO 31

These experiments were carried out with different amines used with the same content by weight (0.1% relative to dichlorophenols).

The operation was performed as in Examples 3 to 6 with the following charges:
- 2,4-dichlorophenol: 21.19 g (130 millimoles)
- 2,6-dichlorophenol: 21.19 g (130 millimoles)
- amine: 0.1% by weight relative to the dichlorophenols
- chlorine: 2.766 liters (123 millimoles).

Table (VI) compiles the characteristics of the different examples, together with the results obtained.

TABLE (VI)

| Examples | Amine Used | DC of the 2,4-DCP | DC of the 2,6-DCP | Y of 2,4,6-TCP | DC of the 2,4-DCP/ DC of the 2,6-DCP |
|---|---|---|---|---|---|
| Example 19 | morpholine | 83.8% | 7.4% | 98% | 11.3 |
| Example 20 | guanidine chlorhydrate | 77.3% | 15.7% | 98.5% | 4.9 |
| Example 21 | acetamidine chlorhydrate | 81.0% | 10.2% | 100% | 7.9 |
| Example 22 | imidazole | 78.2% | 13.4% | 99% | 5.8 |
| Example 23 | DBU(*) | 71.9% | 18.9% | 98% | 3.8 |
| Example 24 | glycine ethyl ester | 79.2% | 12.1% | 99% | 6.5 |
| Example 25 | N—amino-morpholine | 74.3% | 12.7% | 97.2% | 5.8 |
| Example 26 | N—amino-piperidine | 68.8% | 19.4% | 98% | 3.5 |
| Example 27 | N—aminoethyl-pyrrolidine | 81.1% | 10.3% | 97.8% | 7.9 |
| Example 28 | ethanolamine | 84.6% | 8.6% | 98% | 9.8 |
| Example 29 | benzylamine | 82.1% | 8.3% | 98% | 9.9 |
| Example 30 | ethylene-diamine | 61.3% | 27.8% | 98% | 2.3 |
| Example 31 | L-lysine | 63.7% | 25.8% | 96% | 2.5 |

(*)DBU = 1,8-diazabicyclo[5,4,0]7-undecene

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the selective chlorination, at a position ortho to a hydroxyl group thereof, of a phenolic compound having the general formula (I):

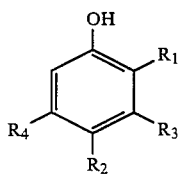

in which $R_2$ is hydrogen, an alkyl radical having from 1 to 4 carbon atoms, an alkoxy radical having from 1 to 4 carbon atoms, an acyloxy radical having from 2 to 4 carbon atoms, an acyl radical having from 2 to 4 carbon atoms, a carboxyl radical, an ester radical —$COOR_5$, wherein $R_5$ is a straight or branched chain alkyl radical having from 1 to 4 carbon atoms, a nitrile radical, an —OH radical, or a —CHO radical; $R_1$ is hydrogen or one of the substituents $R_2$; and $R_3$ and $R_4$, which may be identical or different, are each hydrogen or one of the substituents $R_2$; comprising reacting said compound (I) with gaseous chlorine, in a solvent free, molten reaction medium and at a temperature no greater than about 150° C., in the presence of a catalytically effective amount of a primary, secondary or tertiary amine.

2. The process as defined by claim 1, said amine having the general formula (II):

in which $R_6$, $R_7$ and $R_8$, which may be identical or different, are each a straight chain alkyl radical having from 1 to 12 carbon atoms, a secondary alkyl radical having from 3 to 12 carbon atoms, or a tertiary alkyl radical having from 4 to 12 carbon atoms, with the proviso that such alkyl radicals may contain one or two oxygen bridges, —O—, or a hydroxyl, amine, carboxylic acid, carboxylic acid ester, amide or imine group, a phenyl radical, a cyclohexyl radical, a cycloheptyl radical, a cyclopentyl radical, or a phenylalkyl, cyclohexylalkyl, cycloheptylalkyl or cyclopentylalkyl radical, the alkyl part of which comprises 1 to 4 carbon atoms; with the further proviso that one or two of the substituents $R_6$, $R_7$ and $R_8$ may be hydrogen; $R_6$ may be an $NH_2$ group; $R_7$ and $R_8$ may together form, with the nitrogen atom from which they depend, a heterocycle which is saturated or contains one or several double bonds, or a substituted such heterocycle bearing one or more alkyl substituents having from 1 to 4 carbon atoms; $R_6$, $R_7$ and $R_8$ may together form, with the nitrogen atom from which they depend, an unsaturated heterocycle, or a substituted such heterocycle bearing one or two methyl or ethyl substituents; $R_7$ and $R_8$ or $R_6$, $R_7$ and $R_8$ may together form, with the nitrogen atom from which they depend, and with one or several additional nitrogen and/or oxygen atoms, a saturated or unsaturated heterocycle, optionally substituted by one or several alkyl groups having from 1 to 4 carbon atoms; and $R_7$ and $R_8$ or $R_6$, $R_7$ and $R_8$ may together form with the nitrogen atom from which they depend, and optionally with one or several nitrogen atoms and/or oxygen atoms, a saturated or unsaturated polycyclic compound, optionally substituted by one or several alkyl groups having 1 to 4 carbon atoms.

3. The process as defined by claim 2, the catalytically effective amount of said amine ranging from 0.005% to 5% by weight of the mixture of reaction.

4. The process as defined by claim 2, said amine having the general formula (III):

in which $R_7$ and $R_8$, which may be identical or different, are each hydrogen, with the proviso that both $R_7$ and $R_8$ are not hydrogen, a straight chain alkyl radical having from 1 to 10 carbon atoms, a secondary alkyl radical having from 3 to 10 carbon atoms, a tertiary alkyl radical having from 4 to 10 carbon atoms, a cyclohexyl or cyclopentyl radical, a phenyl radical or a benzyl or phenethyl radical, $R_7$ and $R_8$ may together form, with the nitrogen atom from which they depend, and with another nitrogen atom and/or oxygen atom, a heterocycle which is saturated or which has one or several double bonds, either or both $R_7$ and $R_8$ may contain one or several amine, hydroxyl or carboxylic ester groups.

5. The process as defined by claim 4, said amine (III) being a secondary amine, in which at least one of the substituents $R_7$ and $R_8$ is a secondary alkyl radical having from 3 to 10 carbon atoms, or a secondary amine (III) wherein $R_7$ and $R_8$ form, together with the nitrogen atom from which they depend, a heterocycle optionally containing another nitrogen atom or an oxygen atom.

6. The process as defined by claim 5, in which at least one of the substituents $R_7$ and $R_8$ is isopropyl, 2-butyl, 2-pentyl, 3-pentyl, 2-hexyl, 3-hexyl, 2-heptyl, 3-heptyl, 4-heptyl, 2-octyl, 3-octyl, 4-octyl, 2-nonyl, 3-nonyl, 4-nonyl, 5-nonyl, 2-decyl, 3-decyl, 4-decyl, 5-decyl, cyclohexyl, cyclopentyl, morpholine, or imidiazole.

7. The process as defined by claim 2, said amine (II) being diisopropylamine, diisobutylamine or dicyclohexylamine.

8. The process as defined by claim 2, said amine (II) being n-propylamine, isopropylamine, n-butylamine, isobutylamine, tert-butylamine, n-pentylamine, 2-methylbutylamine, 3-methylbutylamine, n-hexylamine, 2-methylpentylamine, 3-methylpentylamine, 2-ethylhexylamine, laurylamine, cyclohexylamine, cyclopentylamine, benzylamine, glycine ethyl ester, hexamethylenediamine, N-aminoethylpyrrolidine, pyrazoline, N-aminomorpholine N-aminopiperidine or ethanolamine.

9. The process as defined by claim 1, wherein said phenolic compound having the general formula (I), $R_2$ is a chlorine, fluorine or bromine atom, a methoxy or ethoxy radical, an aldehyde radical, an OH radical, a CN radical, an acetoxy radical, an ester radical —$COOR_5$, wherein $R_5$ is a methyl or ethyl radical, or an acyl radical having from 2 to 4 carbon atoms;

$R_1$ is a hydrogen atom, a methyl, ethyl, propyl, isopropyl, or tert-butyl radical, or is one of the substituents $R_2$; and one of $R_3$ and $R_4$ is a hydrogen atom and the other either a hydrogen atom or one of the substituents $R_2$.

10. The process as defined by claim 1, wherein said phenolic compound having the general formula (I) comprises 4-chlorophenol, 2,4-dichlorophenol, 3,4-dichlorophenol, 2-chloro-4-fluorophenol, 4-chloro-2-fluorophenol, 2-bromo-4-chlorophenol, 4-bromo-2-chlorophenol, 2-chloro-4-methoxyphenol, 4-chloro-2-methoxyphenol, 4-chloro-2-methylphenol, 4-methoxyphenol, 4-ethoxyphenol, 4-hydroxyacetophenone, 4-hydroxybenzonitrile, 3-chloro-4-hydroxybenzaldehyde, or 5-chloro-2-hydroxybenzaldehyde.

11. The process as defined by claim 1, wherein said phenolic compound having the general formula (I) comprises mixture of 2,4-dichlorophenol and 2,6-dichlorophenol.

12. The process as defined by claim 1, wherein said phenolic compound having the general formula (I) comprises mixture of 2,4-dichlorophenol, 2,6-dichlorophenol and 2,4,6-trichlorophenol.

13. The process as defined by claim 1, carried out at a temperature from the melting point of the reaction mixture to 120° C.

* * * * *